(12) United States Patent
Schranz et al.

(10) Patent No.: US 12,420,043 B2
(45) Date of Patent: Sep. 23, 2025

(54) VENTILATION DEVICE DESIGNED TO IDENTIFY FUNCTIONAL IMPAIRMENT OF ITS O2 SENSOR ASSEMBLY

(71) Applicant: Hamilton Medical AG, Bonaduz (CH)

(72) Inventors: Christoph Schranz, Fläsch (CH); Jonathan Schad, Bonaduz (CH); Dominik Novotni, Chur (CH); Bernd Offenbeck, Regensburg (DE)

(73) Assignee: Hamilton Medical AG, Bonaduz (CH)

( * ) Notice: Subject to any disclaimer, the term of this patent is extended or adjusted under 35 U.S.C. 154(b) by 573 days.

(21) Appl. No.: 17/923,320

(22) PCT Filed: May 5, 2021

(86) PCT No.: PCT/EP2021/061874
§ 371 (c)(1),
(2) Date: Nov. 4, 2022

(87) PCT Pub. No.: WO2021/224333
PCT Pub. Date: Nov. 11, 2021

(65) Prior Publication Data
US 2023/0233781 A1 Jul. 27, 2023

(30) Foreign Application Priority Data
May 8, 2020 (DE) ...................... 10 2020 112 557.7

(51) Int. Cl.
*A61M 16/00* (2006.01)
*A61B 5/00* (2006.01)
(Continued)

(52) U.S. Cl.
CPC ........... *A61M 16/024* (2017.08); *A61B 5/082* (2013.01); *A61B 5/4848* (2013.01);
(Continued)

(58) Field of Classification Search
CPC ................ A61M 16/024; A61M 16/16; A61M 2016/1025; A61M 2016/103;
(Continued)

(56) References Cited

U.S. PATENT DOCUMENTS 4,986,268 A * 1/1991 Tehrani ................. A61M 16/00
128/204.22
6,000,397 A * 12/1999 Skog .................... A61M 16/085
128/204.22
(Continued)

FOREIGN PATENT DOCUMENTS

DE 102017217859 A1 8/2018

OTHER PUBLICATIONS

International Search Report for corresponding PCT/EP2021/061874 mailed Aug. 9, 2021, 16 pgs.
(Continued)

*Primary Examiner* — Tu A Vo
(74) *Attorney, Agent, or Firm* — Rankin, Hill & Clark LLP

(57) ABSTRACT

A ventilation device for artificial ventilation, having: —a ventilation gas source; —a ventilation line arrangement; —a pressure-changing assembly for changing the pressure of the ventilation gas flowing in the ventilation line arrangement; —a control device; —an evaluation device for processing sensor signals; and —an O2 sensor assembly for determining an O2 concentration value representing the oxygen concentration of the ventilation gas flowing in the ventilation line arrangement, wherein the O2 sensor assembly outputs O2 sensor signals, which contain information regarding the O2 concentration value, to the evaluation device, and wherein the evaluation device is designed to determine, on the basis of the O2 sensor signals, an O2 change value representing a change in the O2 concentration
(Continued)

value and, if the O2 change value satisfies a predefined condition, to infer degradation of the O2 sensor assembly and to output a signal.

22 Claims, 5 Drawing Sheets

(51) Int. Cl.
| | |
|---|---|
| *A61B 5/08* | (2006.01) |
| *A61M 16/04* | (2006.01) |
| *A61M 16/08* | (2006.01) |
| *A61M 16/10* | (2006.01) |
| *A61M 16/16* | (2006.01) |
| *A61M 16/20* | (2006.01) |

(52) U.S. Cl.
CPC .... *A61M 16/0051* (2013.01); *A61M 16/1005* (2014.02); *A61B 2505/03* (2013.01); *A61B 2505/05* (2013.01); *A61M 2016/0036* (2013.01); *A61M 16/0069* (2014.02); *A61M 16/04* (2013.01); *A61M 16/0808* (2013.01); *A61M 16/0833* (2014.02); *A61M 16/0883* (2014.02); *A61M 2016/1025* (2013.01); *A61M 2016/103* (2013.01); *A61M 16/107* (2014.02); *A61M 16/16* (2013.01); *A61M 16/202* (2014.02); *A61M 2205/3313* (2013.01); *A61M 2205/3358* (2013.01); *A61M 2205/581* (2013.01); *A61M 2205/582* (2013.01); *A61M 2205/583* (2013.01); *A61M 2205/702* (2013.01); *A61M 2205/7545* (2013.01); *A61M 2230/432* (2013.01); *A61M 2230/435* (2013.01)

(58) Field of Classification Search
CPC .......... A61M 16/0051; A61M 16/0069; A61M 16/04; A61M 16/0808; A61M 16/0833; A61M 16/0883; A61M 16/107; A61M 16/202; A61M 2016/0036; A61M 2205/3313; A61M 2205/583; A61M 16/1005; A61M 2205/3358; A61M 2205/581; A61M 2205/582; A61M 2205/702; A61M 2205/7545; A61M 2230/432; A61M 2230/435; A61B 2505/03; A61B 2505/05; A61B 5/082; A61B 5/4848

See application file for complete search history.

(56) References Cited

U.S. PATENT DOCUMENTS

| | | | |
|---|---|---|---|
| 6,095,986 A | 8/2000 | Braig et al. | |
| 7,833,480 B2 | 11/2010 | Blazewicz et al. | |
| 8,021,615 B2* | 9/2011 | Mueller | C07C 2/64 436/164 |
| 8,448,642 B2 | 5/2013 | Tappehorn et al. | |
| 2004/0107965 A1* | 6/2004 | Hickle | A61M 16/085 128/204.22 |
| 2007/0062529 A1* | 3/2007 | Choncholas | A61M 16/205 128/204.22 |
| 2011/0041848 A1* | 2/2011 | Stone | B63C 11/12 128/203.14 |
| 2011/0302992 A1* | 12/2011 | Robbins | G01N 21/05 73/23.3 |
| 2014/0127081 A1* | 5/2014 | Fine | A61M 16/12 422/198 |
| 2015/0328417 A1* | 11/2015 | Löser | A61M 16/024 128/204.23 |
| 2016/0184545 A1 | 6/2016 | Kauppi | |
| 2020/0072738 A1 | 3/2020 | Giardina et al. | |
| 2020/0359935 A1 | 11/2020 | Clemensen et al. | |
| 2021/0223176 A1 | 7/2021 | Schönfuss et al. | |
| 2021/0322709 A1* | 10/2021 | Kopalli | A61M 16/0051 |

OTHER PUBLICATIONS

German Search Report for corresponding DE 10 2020 112 557.7 mailed Jan. 25, 2021, 5 pgs.
Espacenet Bibliographic data: DE 102017217859 (A1), Published Aug. 16, 2018, 1 pg.
International Preliminary Report On Patentability for corresponding PCT/EP2021/061874 mailed Nov. 8, 2022, 9 pgs.

* cited by examiner

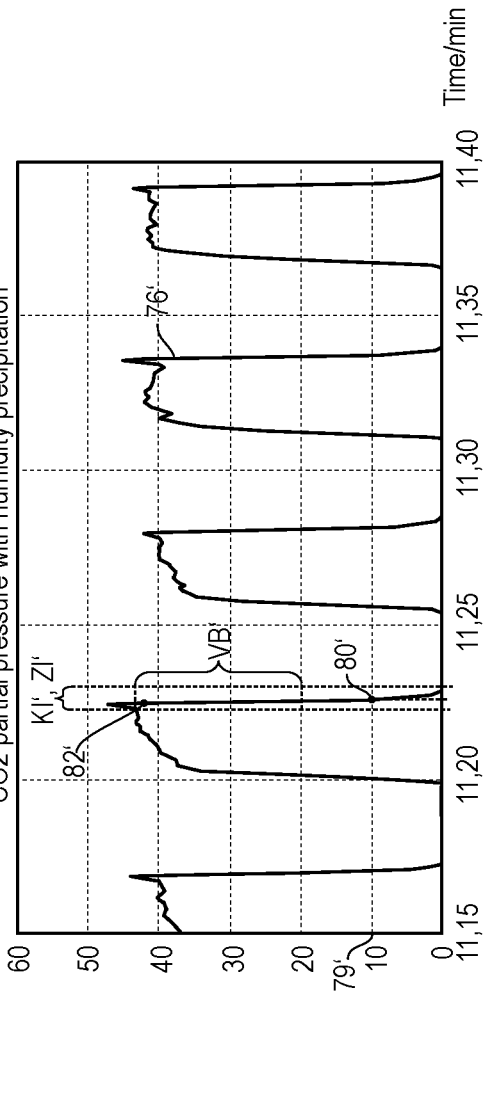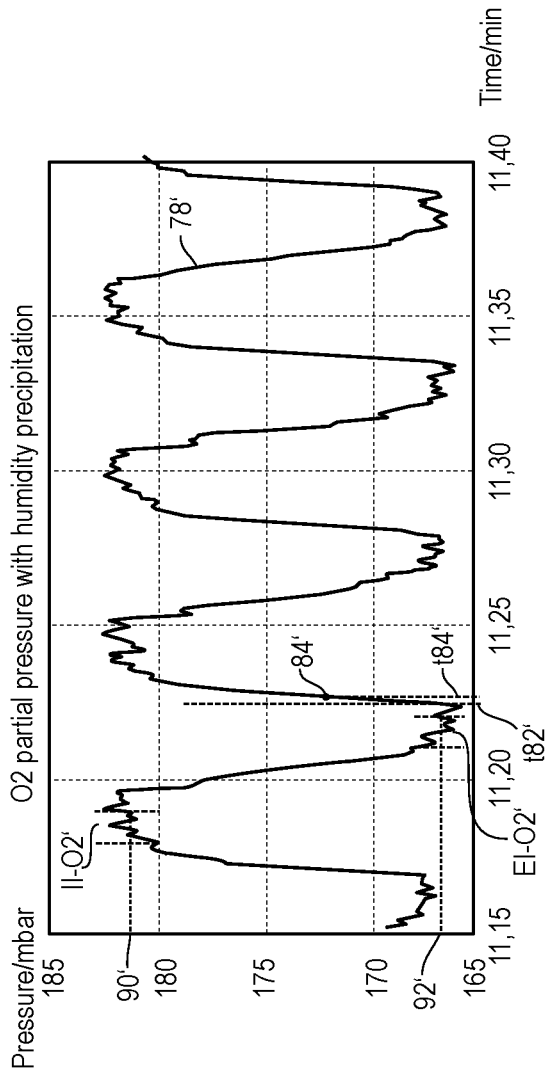
Fig. 4A
Fig. 4B

VENTILATION DEVICE DESIGNED TO IDENTIFY FUNCTIONAL IMPAIRMENT OF ITS O2 SENSOR ASSEMBLY

This application claims priority in PCT application PCT/EP2021/061874 filed on May 5, 2021, which claims priority in German Patent Application DE 10 2020 112 557.7 filed on May 8, 2020, which are incorporated by reference herein.

The present invention concerns a ventilation device for artificial respiration, comprising A respiratory gas source, A ventilation line arrangement in order to lead inspiratory respiratory gas from the respiratory gas source to a patient-side proximal respiratory gas outlet aperture and in order to lead expiratory respiratory gas away from a proximal respiratory gas inlet aperture, A pressure modification arrangement for modifying the pressure of the respiratory gas flowing in the ventilation line arrangement, A control device designed to control the operation of the respiratory gas source and/or of the pressure modification arrangement, An evaluation device for processing sensor signals, and An $O_2$ sensor assembly for ascertaining an $O_2$ content value which represents an oxygen content of the respiratory gas flowing in the ventilation line arrangement, where the $O_2$ sensor assembly outputs to the evaluation device $O_2$ sensor signals which contain information about the $O_2$ content value.

BACKGROUND OF THE INVENTION

A ventilation device for artificial respiration with a respiratory gas source, a ventilation line arrangement, a pressure modification arrangement, and a control device is known for example from DE 10 2017 204 082 A1. From this publication there is moreover known an $O_2$ sensor assembly working according to the luminescence extinction principle. Here, a luminophore-containing material is excited by a radiation source to emit light. The excited light-emitting behavior detected by a detection device depends on the quantity of oxygen which as a component of the respiratory gas comes into contact with the excited luminophore. Oxygen molecules coming into contact with the excited luminophore de-excite the luminophore, thus decreasing its light-emitting intensity and/or duration. The greater the oxygen fraction in the respiratory gas, the stronger the resulting de-excitation of the luminophore.

From DE 10 2018 207 666 A1 there is known a further $O_2$ sensor working according to the luminescence extinction principle, which for deployment at a ventilation line arrangement is designed for ascertaining an oxygen content of the respiratory gas flowing in the ventilation line arrangement.

Moreover, often ventilation devices exhibit a $CO_2$ sensor assembly in order to detect $CO_2$ contained in the respiratory gas. In order to identify a $CO_2$ fraction of a respiratory gas, infrared spectroscopic sensor assemblies are known which shine infrared light through a respiratory gas flow and based on the absorption of infrared light by carbon dioxide, allow in a manner which is known per se the identification of the carbon dioxide content in the respiratory gas. Such capnometric infrared sensor assemblies are known for example from U.S. Pat. No. 6,095,986 A, GB 2 533 806 B, and DE 10 2006 052 999 A1.

The respiratory gas exhibits a certain humidity, which under adverse thermal conditions can precipitate as a fluid on solid surfaces in the ventilation line arrangement and likewise in the sensor assemblies through which respiratory gas flows. This is the case both for inspiratory respiratory gas, which is conditioned with regard to its humidity level in order to be as tolerable as possible for the patient, and for expiratory respiratory gas, which in addition can be augmented by body fluids released by the patient via the respiratory tract, such as for instance saliva and mucus.

Whereas often precipitated humidity does not especially impair the measurement accuracy of infrared spectroscopic $CO_2$ sensor assemblies and/or any impairment can be readily compensated for, humidity precipitation constitutes a considerable problem for $O_2$ sensor assemblies. Since the identifications of the carbon dioxide content and of the oxygen content in the respiratory gas are utilized for assessing the metabolizing of the respiratory gas by the patient and consequently can impact the respiratory parameters of the artificial respiration, the identification of the carbon dioxide content and of the oxygen content in the respiratory gas with the highest possible accuracy is of special interest.

From U.S. Pat. No. 7,833,480 B2 there is known a further $O_2$ sensor assembly working according to the luminescence extinction principle. This publication mentions the sensitivity of the known $O_2$ sensor assembly to humidity. In order to counter the impact of humidity on the function of the known $O_2$ sensor assembly, U.S. Pat. No. 7,833,480 B2 merely mentions generally the use of compensation algorithms to compensate for measurement errors caused by. The compensation algorithms themselves are explained in the publication in further detail neither through direct clarification nor through reference to appropriate sources. It is conceivable that the device known from U.S. Pat. No. 7,833,480 B2 uses a humidity sensor in order to compensate, depending on its signal, for the $O_2$ sensor signals of the known $O_2$ sensor assembly.

SUMMARY OF THE INVENTION

The task of the present invention, therefore, is to propose a ventilation device which is not only able to ascertain an oxygen content in the respiratory gas, but which is also able to check the $O_2$ sensor assembly provided for ascertaining the oxygen content for impairments caused by precipitated humidity and if required to inform a user of the ventilation device accordingly.

According to the present invention, this task is solved by a ventilation device as proposed at the beginning, in which the evaluation device is designed to determine, based on the $O_2$ sensor signals, an $O_2$ change value representing a change in the $O_2$ content value and when the $O_2$ change value satisfies a predetermined condition, conclude that there exists degradation of the $O_2$ sensor assembly and output a signal.

Preferably the $O_2$ sensor assembly is a sensor assembly working according to the luminescence extinction principle. Such sensor assemblies and their mode of operation are described in detail in the aforementioned state of the art and are assumed to be known. The $O_2$ sensor assembly can, however, be an arbitrary other $O_2$ sensor assembly relying on the contact of oxygen molecules with a reaction substance and/or a catalytic substance. Merely for the sake of illustration, the example of a sensor assembly working according to the luminescence extinction principle is used below in describing the invention.

The observation region of such an $O_2$ sensor assembly in a ventilation line arrangement, which region is observable in order to ascertain the oxygen content and is equipped with an excitable luminophore, is constructed as follows, in general lines: Towards the flow chamber of the respiratory gas there is arranged an oxygen-permeable carrier substrate layer referred to hereunder as a 'membrane', which carries a luminophore capable of being excited to luminesce. The luminophore can be embedded in a material of the carrier substrate acting as a matrix or can be applied on the side facing away from the flow chamber of the respiratory gas as a luminophore layer. Since the respiratory gas can bathe the side of the oxygen-permeable membrane which faces towards it, oxygen contained in the respiratory gas can reach the luminophore of the $O_2$ sensor assembly and extinguish its excited luminescence.

On the side facing away from the flow chamber of the respiratory gas, the luminophore is covered by an oxygen-impermeable covering layer in order to prevent oxygen of the ambient air contributing to the extinguishing of the excited luminescence and thus falsifying the result which should provide information only about the oxygen content of the respiratory gas.

Humidity and/or liquid carried along by the respiratory gas and precipitating on the side of the observation region facing towards the flow chamber, prevents or impedes the oxygen contained in the respiratory gas reaching the luminophore to an extent which corresponds to the oxygen fraction in the respiratory gas and consequently effecting an extinction of the excited luminescence of the luminophore which corresponds to its fraction in the respiratory gas.

In this process, a liquid film can cover the membrane towards the flow chamber partly or even completely, and/or due to a capillary effect, liquid precipitating on the membrane can migrate into the oxygen-permeable membrane, thereby filling up its porosity partly or completely. As a result, a lower oxygen content of the respiratory gas is ascertained by a thus liquid-loaded $O_2$ sensor assembly than the actual oxygen content, namely the stronger the liquid loading, the lower the ascertained content. More accurately, due to the undesirable liquid loading a change in the oxygen content is detected as slower than the way in which it actually takes place. Over a limited detection period, such as for instance an inspiratory phase or an expiratory phase, the change in the oxygen content, detected as slower than it actually is, results in an $O_2$ content value which represents a quantitatively lower oxygen content than the actual one.

Since the oxygen in the patient's lung is metabolized to carbon dioxide, the carbon dioxide content in the expiratory respiratory gas is greater than in the inspiratory respiratory gas and the oxygen content in the inspiratory respiratory gas greater than in the expiratory respiratory gas. Consequently, on the one hand both the carbon dioxide content and the oxygen content of the respiratory gas change between the respiratory part-phases: the inspiratory phase and the expiratory phase. On the other, an $O_2$ content value also changes within a respiratory part-phase and a $CO_2$ content value also changes within a respiratory part-phase, in particular within an expiratory phase.

Within the meaning of the present application, a breath comprises an expiratory phase and an inspiratory phase, where one phase immediately follows the other. Here the order of the phases does not matter.

What is problematic in the present detection situation is that the $O_2$ sensor assembly always provides $O_2$ sensor signals, but regarding which it is not at first clear whether they are the result of a correct detection. For assessing an impairment of the $O_2$ sensor assembly, the present invention does not focus on the $O_2$ sensor signals themselves or on the respective $O_2$ content value represented by each of them, but rather relies on the change behavior of the $O_2$ sensor signals and of the $O_2$ content value represented by them. From the change behavior it is possible in various ways to obtain data about a liquid loading of the $O_2$ sensor assembly.

In order to prevent as far as possible an erroneous output by the evaluation device of a signal indicating a degradation of the $O_2$ sensor assembly, preferably the evaluation device is designed to output the signal only if the predetermined condition is satisfied a predetermined plurality of times within a predetermined plurality of breaths. This makes possible a secure assessment of an impairment of the $O_2$ sensor assembly in what is still a very short time. For example, the signal can only be output if the condition is satisfied three times over at least three breaths.

Preferably there is performed for one breath exactly one verification procedure for verifying the functionality of the $O_2$ sensor assembly. Therefore, preferably the number of required fulfilment events of the condition equal to the predetermined plurality of breaths.

For the fastest possible detection of an impairment of the $O_2$ sensor assembly, preferably each fulfilment of the condition over not more than ten breaths is advantageous. In tests, fulfilment of the predetermined condition five times over five breaths has proved especially to be a very good compromise between accurate and rapid detection of the impairment of the $O_2$ sensor assembly. In order to keep the time until recognition of the impairment as short as possible, the breaths of the plurality of breaths follow one another directly, although this is not imperative.

As will be elucidated below in greater detail, in a verification procedure for identification by the evaluation device of an impairment of the $O_2$ sensor assembly there can be checked exactly one predetermined condition or also a plurality of different predetermined conditions, for instance two predetermined conditions, namely the difference criterion of the first embodiment and the gradient criterion of the second embodiment. However, preferably in this process it suffices if only exactly one of the checked conditions is satisfied.

In the same way, the evaluation device be designed to output, after the output of a signal indicating the impairment of the $O_2$ sensor assembly, a further signal indicating the rectification of the impairment if the predetermined condition or, in the case of a plurality of checked conditions, if every condition out of a plurality of conditions is not satisfied a predetermined plurality of times within a predetermined plurality of breaths.

The evaluation device can be formed by the control device or a part of the control device. Preferably the evaluation device and/or the control device comprises an integrated circuit for performing data-processing operations and a data memory for retrievable storage of data to be processed. The evaluation device can completely or at least in part be located at least at one of the sensor assemblies, since in the housing of a sensor assembly too, electronic circuits can be arranged for signal storage and signal processing of the respective at least one detecting sensor element of the sensor assembly. In order to ensure provision and/or output of the most defined sensor information possible, preferably in each case at least one part of the evaluation device is arranged at the $O_2$ sensor assembly, as likewise at the $CO_2$ sensor assembly mentioned further below. This evaluation device or part-evaluation device processes sensor signals of the respective allocated sensor assembly and outputs processed or preprocessed sensor signals to a further part of the evaluation device, if present, or to the control device.

According to a first embodiment of the present invention, the evaluation device can be designed to ascertain, based on the $O_2$ sensor signals, an $O_2$ difference value as the $O_2$ change value. This $O_2$ difference value represents a quantitative difference between a characteristic expiratory $O_2$ content value of the expiratory respiratory gas and a characteristic inspiratory $O_2$ content value of the inspiratory respiratory gas. The predetermined condition is that the $O_2$ difference value is related in a predetermined relative relationship to an $O_2$ difference limit. This condition and its further developments are referred to in the present application as 'difference criterion'.

By 'predetermined relative relationship' there is denoted a comparative relationship such as 'greater than', 'smaller than', 'greater than or equal to', and 'smaller than or equal to'. The specifically appropriate relative comparative relationship depends on the specifically employed definition of the $O_2$ difference value.

By the attribute 'characteristic' there is merely expressed that the characteristic $O_2$ content value thus denoted is selected or determined or calculated according to predetermined rules from a plurality of available $O_2$ content values of a breath or a respiratory part-phase.

According to the difference criterion of the first embodiment, a response characteristic which indicates an impairment of the $O_2$ sensor assembly is preferably expressed by the magnitude of the $O_2$ difference value not exceeding a predetermined $O_2$ difference limit. This difference criterion is based on the awareness that a liquid-loaded $O_2$ sensor assembly continues to detect an oxygen content in the respiratory gas, but this is likely to be quantitatively too low. The ratio of the ascertained oxygen contents of expiratory and inspiratory respiratory gas to each other can be nearly unaffected by the impairment. However, given sufficient impairment of the $O_2$ sensor assembly, the quantitative gap between the oxygen content of the inspiratory respiratory gas and the oxygen content of the expiratory respiratory gas decreases. The difference criterion based on the $O_2$ difference value reflects this circumstance, such that the $O_2$ sensor assembly is deemed to be degraded or more precisely impaired if the quantitative gap between the oxygen content of the inspiratory respiratory gas and the oxygen content of the expiratory respiratory gas is quantitatively too small.

Depending on whether the unsigned magnitudes of difference values or the signed difference values are being considered, the predetermined relative relationship of a difference value to the difference limit associated with it changes in the case of negative difference values, when compared with using only their magnitudes.

When applying the difference criterion, the accuracy of the assessment of the functionality of the $O_2$ sensor assembly can be increased by taking the ambient atmosphere into account. Normally, the $O_2$ sensor assembly outputs $O_2$ sensor signals which starting from the applied measurement principle, represent the $O_2$ partial pressure in the respiratory gas as the prevailing $O_2$ content value. Given knowledge of the atmospheric pressure as a preferred example of an atmospheric state value, the significance of the content values obtained as partial pressures can be more appropriately evaluated. The evaluation device is therefore preferably designed to take into account, when performing the comparison of an $O_2$ difference value with an $O_2$ difference limit, at least one atmospheric state value which represents a state of the ambient atmosphere of the ventilation device.

According to a first alternative, this taking into account of the atmospheric state value, preferably of the atmospheric pressure, can take place through the evaluation device by the evaluation device ascertaining the $O_2$ difference limit as a function of the at least one atmospheric state value. For example, the evaluation device can form the product of the $O_2$ difference limit and the atmospheric state value as an $O_2$ difference limit which takes the atmospheric state into account.

According to one alternative, the evaluation device can take the atmospheric state value into account by the evaluation device ascertaining an atmosphere-based $O_2$ difference value from the $O_2$ difference value and the at least one atmospheric state value. For example, the evaluation device can form the ratio of the $O_2$ difference value to the at least one atmospheric state value as an atmosphere-based $O_2$ difference value.

In ventilation technology, pressures have proved reliable as state values of gases, which is why preferably the at least one atmospheric state value represents the atmospheric pressure, the $O_2$ difference value represents an $O_2$ partial pressure difference value between an $O_2$ partial pressure in the expiratory respiratory gas and an $O_2$ partial pressure in the inspiratory respiratory gas. As already described above, partial-pressure-proportional $O_2$ sensor signals can be obtained directly by means of the physical operating principles on which the available $O_2$ sensor assemblies rely in their mode of operation.

An atmosphere-based difference value does not, however, have to be formed from the same physical variables, but instead can be a mere numerical value formed through mathematical linking of different physical variables.

In order to use the most informative $O_2$ content values possible when applying the difference criterion, the former should not be determined too near to the beginning or the end of their respiratory part-phase. Therefore, the characteristic inspiratory $O_2$ content value preferably derives from an inspiratory phase segment which is located at a first temporal distance from the beginning of an inspiratory phase and at a second temporal distance from the end of the inspiratory phase. Additionally or alternatively, the characteristic expiratory $O_2$ content value preferably derives from an expiratory phase segment which is located at a third temporal distance from the beginning of an expiratory phase and at a fourth temporal distance from the end of the expiratory phase.

Preferably, the first to fourth temporal distances are chosen to be so large that the $O_2$ content values are not determined in the transient segments of the respective respiratory part-phase in which the $O_2$ content values change considerably in magnitude within short time increments, i.e. for example not in the rising and falling flanks of an $O_2$ content curve which describes the $O_2$ content over time.

Since the determination, as described here, of an impairment of the $O_2$ sensor assembly is performed during the ongoing ventilation operation, it is advantageous if the determination of the functionality utilizes as few system resources of the ventilation device as possible. A determination in the shortest possible time and with the smallest possible cost in computing power can, for example, be supported by the evaluation device being designed to identify the aforementioned inspiratory phase segment and/or the aforementioned expiratory phase segment and only therein ascertain a characteristic $O_2$ content value. Consequently, the characteristic $O_2$ content value does not have to be ascertained over the entire inspiratory phase and/or over the entire expiratory phase, respectively, and consequently a relatively large data quantity be processed. For example, as an expiratory phase segment there can be identified a predetermined time segment which starts a predetermined time interval after the beginning of the expiratory phase and lasts for a predetermined time interval. In such an expiratory phase segment as a normally plateau-like respiratory part-phase segment with, compared with the transient segments at the beginning and at the end of a respiratory part-phase, quantitatively relatively small changes in the $O_2$ sensor signal—but not only in such a respiratory part-phase segment—a characteristic expiratory $O_2$ content value can be determined as the average of a plurality of $O_2$ content values. The equivalent applies to the inspiratory phase segment as the respective other respiratory part-phase segment.

Every respiratory part-phase usually displays, with regard to the gas fractions discussed here: oxygen and carbon dioxide, an initial transient segment with a rapid rise of the gas content value in the respiratory gas. The transient segment is followed by a plateau segment with quantitatively small changes in the gas content value, which fluctuates about a certain level in the plateau segment. The plateau segment is followed by a final transient segment, in which the gas content value decreases rapidly.

The beginning and/or the end of a respiratory part-phase can be ascertained from the detected respiratory gas flows in the ventilation line arrangement. In order to detect respiratory gas flows, the ventilation device preferably exhibits in the ventilation line arrangement a flow sensor, for instance a flow sensor working according to the differential pressure principle or a hot-wire sensor. Alternatively or additionally, the beginning or the end of a respiratory part-phase can be determined from a detection of an operation of the pressure modification arrangement, for example from an operating position of an inspiratory valve and of an expiratory valve or from an operation of a fan of the pressure modification arrangement.

Alternatively, a respiratory part-phase segment for determining a characteristic $O_2$ content value can be ascertained independently of a predetermined time interval on the basis of a predetermined threshold value, for instance on the basis of a predetermined temporal distance to the event of reaching a threshold value. The predetermined temporal distance can also be zero. In this way, a beginning or an end of a respiratory part-phase segment can be recognized, based on the event that an $O_2$ sensor signal exceeds an $O_2$ inspiratory threshold value during an inspiratory phase, which indicates that a transient segment ends at the beginning of the inspiratory phase and/or an $O_2$ sensor signal falls below an $O_2$ expiration threshold value during an expiratory phase, which indicates that a plateau segment of the expiratory phase ends with a merely minor quantitative change in the $O_2$ sensor signals and changes over into a transient segment at the end of the expiratory phase.

In order to be able to detect, by means of the ventilation device, the metabolizing of oxygen in the patient's lung, the ventilation device additionally exhibits according to a preferred further development a $CO_2$ sensor assembly designed for ascertaining a $CO_2$ content value which represents a carbon dioxide content of the respiratory gas flowing in the ventilation line arrangement, where the $CO_2$ sensor assembly outputs to the evaluation device $CO_2$ sensor signals which contain information about the $CO_2$ content value.

According to a second embodiment of the present invention, which can be realized alternatively or preferably additionally to the above first embodiment, the evaluation device can be designed to ascertain from the $CO_2$ sensor signals a $CO_2$ gradient value which represents a temporal change in the carbon dioxide content in the expiratory respiratory gas. The change in the carbon dioxide content in the expiratory respiratory gas equals the change in the $CO_2$ content value in an expiratory phase. According to this second embodiment, the evaluation device is further designed to ascertain, as the $O_2$ change value, an $O_2$ gradient value which represents a temporal change in the oxygen content in the inspiratory respiratory gas. The change in the oxygen content in the inspiratory respiratory gas equals the change in the $O_2$ content value in an inspiratory phase. The aforementioned predetermined condition is then, that a ratio of the $CO_2$ gradient value to the $O_2$ gradient value is related in a predetermined relative relationship to a change ratio limit. This condition and its further developments are referred to in the present application as 'gradient criterion'. According to the second embodiment, therefore, the evaluation device is designed to deduce a degradation of the $O_2$ sensor assembly and to output an appropriate signal when a ratio of the $CO_2$ gradient value to the $O_2$ gradient value is related in a predetermined relative relationship to a change ratio limit.

As regards the term 'predetermined relative relationship', what has already been said above applies.

The limits named in the present application, such as in particular difference limit and change limit, can be determined in the laboratory in advance.

In a description which is considerably simplified for elucidation purposes, the gradient criterion is a means for assessing whether changes in the carbon dioxide content in the expiratory respiratory gas and changes in the oxygen content in the inspiratory respiratory gas match each other quantitatively to a sufficiently plausible degree: If the $O_2$ gradient value changes, for instance because the liquid-loaded $O_2$ sensor assembly detects a lesser amount of oxygen and therefore with a lesser temporal change than without liquid loading, without the $CO_2$ gradient value changing, the evaluation device can then deduce a degradation of the $O_2$ sensor assembly when the ratio of the magnitude of the $CO_2$ gradient value to the magnitude of the $O_2$ gradient value is greater than the change ratio limit. This is equivalent to the ratio of the magnitude of the $O_2$ gradient value to the magnitude of the $CO_2$ gradient value being smaller than a further change ratio limit, where the further change ratio limit is the inverse of the aforementioned change ratio limit. Because of this unambiguous relationship, hereunder only the aforementioned change ratio limit will be discussed.

Although in a less preferable embodiment of the invention it can suffice to use only one of the two aforementioned criteria out of the difference criterion and the gradient criterion for determining an impairment of the $O_2$ sensor assembly, the ventilation device according to the invention preferably uses both criteria for determining an impairment of the $O_2$ sensor assembly with the objective of having the most reliable detection possible of a degradation of the $O_2$ sensor assembly, where satisfying one of the assessment criteria out of the difference criterion and the gradient criterion already indicates an impairment of the $O_2$ sensor assembly and can suffice for the output of a corresponding signal.

In order to be able to detect a degradation of the $O_2$ sensor assembly as early as possible, the evaluation device preferably performs iteratively during a ventilation operation a verification procedure for determining an impairment of the $O_2$ sensor assembly, preferably in a rhythm correlated functionally with the ventilation rhythm, for instance for every nth breath, where n is a natural number. Especially preferably, n=1 such that a verification procedure is performed for every breath.

The signal output by the evaluation device on detecting a degradation of the $O_2$ sensor assembly can be a signal perceivable by a user in the external environment of the ventilation device, such as for instance an acoustic and/or visual and/or haptic signal, such that the user obtains knowledge of the detected degradation as rapidly as possible. The signal can alternatively or additionally be a data signal which the evaluation device outputs to another device for further signal processing by the latter, for instance to the control device or to a segment of the control device.

In principle, the $CO_2$ gradient value can be determined in an arbitrary transient segment of an expiratory phase, i.e. at the beginning of an expiratory phase or towards the end of the expiratory phase. In the transient segments, the $CO_2$ content value changes quantitatively with time especially strongly, such that in a transient segment an especially distinct $CO_2$ gradient value can be ascertained.

Experiments thus far have shown that the carbon dioxide content in the expiratory respiratory gas as a function of time, with otherwise unchanged ventilation parameters, provides value runs in the relevant end segments of expiratory phases that agree with each other better than in the relevant start segments of expiratory phases. In other words: the falling flanks of a carbon dioxide content curve as a function of time in a specified ventilation operation are in agreement, under constant ventilation parameters, better than the rising flanks of the same curve. For this reason, the evaluation device is preferably designed to determine the $CO_2$ gradient value in the end segment of an expiratory phase and/or in the changeover segment from an expiratory phase to an inspiratory phase respectively, that is, in the falling flank or flanks respectively of a carbon dioxide content curve which shows the carbon dioxide content of the respiratory gas over the ventilation period. The $CO_2$ gradient value is therefore preferably a value of a change in the carbon dioxide content, more specifically in the $CO_2$ content value representing it, towards smaller values.

Since the ventilation device can end an expiratory phase by supplying inspiratory respiratory gas to the patient, the end segment of an expiratory phase can overlap temporally with the start segment of an inspiratory phase. Since an expiratory process begins by respiratory gas present in the patient's lung under pressure beginning to flow out of the patient's lung away from the patient against the quantitatively decreasing flow of inspiratory respiratory gas, the end segment of an inspiratory phase can also overlap with the start segment of an expiratory phase.

The $CO_2$ gradient value can be ascertained by the evaluation device in a variety of ways, for instance in the manner of a gradient triangle by subtracting a temporally earlier $CO_2$ content value from a temporally later $CO_2$ content value and dividing the result of the subtraction by the temporal distance between the two $CO_2$ content values. Alternatively or additionally, the temporal course of a carbon dioxide content curve and/or of a $CO_2$ content value curve respectively, can, based on $CO_2$ sensor signals obtained at different times, be approximated at least segment-wise by an analytical mathematical function and the function differentiated in respect of time for ascertaining the $CO_2$ gradient value. The equivalent applies to determining the $O_2$ gradient value.

In principle, a mean value ascertained over a plurality of $CO_2$ gradient values lying in a predetermined time interval can also be ascertained as the $CO_2$ gradient value. However, it has proved advantageous when using the gradient criterion to utilize the $CO_2$ gradient value as a reference value for determining the $O_2$ gradient value. Consequently, a $CO_2$ gradient value is preferable to which a point in time of its occurrence can be assigned with sufficient accuracy.

Preferably, therefore, the evaluation device is designed to determine a characteristic $CO_2$ gradient value as a reference value. This can be an extreme value of a $CO_2$ gradient value occurring in a predetermined segment of the expiratory phase. This extreme value can be a local or an absolute extreme value in a transient segment of an expiratory phase. If, for example, in a certain ventilation operation there occur a plurality of local extreme values of the $CO_2$ gradient value in the transient segment, the kth occurring local extreme value can be utilized as the characteristic $CO_2$ gradient value, where k is a predetermined natural number.

Within a predetermined segment of an expiratory phase, ascertaining an absolute extreme value as the characteristic $CO_2$ gradient value is preferred because of the uniqueness of the reference value thus ascertained. Therefore, in accordance with the above remarks, the evaluation device is preferably designed, on the basis of a plurality of $CO_2$ sensor signals of a breath, in particular on the basis of a plurality of $CO_2$ sensor signals of an expiratory phase, to ascertain the quantitatively largest temporal change in the carbon dioxide content towards decreasing values as the $CO_2$ gradient value.

In order to determine the $O_2$ gradient value, the evaluation device can be designed to use the point in time of the occurrence of the $CO_2$ gradient value as a reference point in time, and on the basis of a plurality of $O_2$ sensor signals of a breath to use a change value of the oxygen content as the $O_2$ gradient value which occurs in a predetermined temporal distance from the $CO_2$ gradient value. The temporal distance can be a predetermined temporal distance or can be determined for the respective ventilation operation on the basis of ventilation parameters, in particular the ventilation frequency.

In principle, the $O_2$ gradient value can also be ascertained in an arbitrary transient segment of a breath, in particular in an inspiratory phase. Here it has transpired that a degradation of the $O_2$ sensor assembly just at the beginning of an inspiratory phase manifests itself especially clearly if the oxygen content in the respiratory gas increases starting from the low value of an expiratory phase. Preferably, therefore, for achieving especially reliable assessment results with regard to a degradation of the $O_2$ sensor assembly, it is provided that the predetermined temporal distance is chosen in such a way that the $O_2$ gradient value lies in a start segment of an inspiratory phase or, because of the aforementioned possibility of temporal overlapping of the inspiratory phase and the expiratory phase, in a segment of a changeover from an expiratory phase to an inspiratory phase. In such segments, the oxygen content increases with time.

Thus, preferably the $CO_2$ gradient value occurs temporally before the $O_2$ gradient value.

As already described above, preferably the $CO_2$ gradient value lies in an end segment of an expiratory phase or in a segment of a changeover from an expiratory phase to an inspiratory phase. In order to utilize the most informative $CO_2$ and $O_2$ change values possible for assessing the impairment of the $O_2$ sensor assembly, it is advantageous if the ascertained gradient values of $CO_2$ and $O_2$ are not too far apart in time. For a conventional ventilation of an adult patient, the predetermined temporal distance between the $CO_2$ gradient value and the $O_2$ gradient value associated with it lies in a range from 25 to 80 ms, preferably in a range from 35 to 65 ms, especially preferably in a range from 45 to 55 ms. Then the $O_2$ gradient value lies in an inspiratory process which immediately follows the expiratory process in which the $CO_2$ gradient value lies.

Since the characteristic $CO_2$ gradient value is preferably utilized as a reference value for the verification procedures of the present invention, the evaluation device can further, alternatively to the embodiments already presented above, be designed to identify the respiratory part-phase segments: inspiratory phase segment and/or expiratory phase segment, for determining the characteristic inspiratory $O_2$ content value and/or the characteristic expiratory $O_2$ content value based on the aforementioned characteristic $CO_2$ gradient value. According to a preferred embodiment, the evaluation device can be designed to ascertain the inspiratory phase segment and/or the expiratory phase segment as a function of the temporal determination of the occurrence of the quantitatively largest temporal change in the carbon dioxide content and/or in the $CO_2$ content value respectively towards decreasing values. This is advantageous first and foremost when the evaluation device, as is preferable, uses the difference criterion and the gradient criterion for ascertaining an impairment of the $O_2$ sensor assembly, such that a quantitative maximum of the temporal change in the carbon dioxide content and/or in the $CO_2$ content value respectively towards decreasing values as the characteristic gradient value is ascertained anyway and is then present.

In order to minimize the system resources required for determining an impairment of the $O_2$ sensor assembly, when using the gradient criterion as likewise previously when using the difference criterion the evaluation device can be designed to identify an examination time interval in an end segment of an expiratory process and/or in a changeover segment from an expiratory phase to an inspiratory phase respectively and to search only within the examination time interval for an occurrence of the quantitatively largest temporal change in the carbon dioxide content and/or in the $CO_2$ content value respectively towards decreasing values. This considerably reduces the computational cost necessary for determining the quantitatively largest temporal change in the carbon dioxide content.

Since normally a valid, i.e. suitable examination time interval adjoins the aforementioned plateau segment, the aforementioned criteria for identifying the respiratory part-phase segments when using the difference criterion can also be utilized for identifying the examination time interval when using the gradient criterion. Consequently, the evaluation device can be designed, in order to identify the examination time interval from a plurality of $CO_2$ sensor signals as a triggering event, to determine when the $CO_2$ content value falls below a predetermined $CO_2$ triggering limit, and starting from the ascertained triggering time event to define a time interval as a candidate interval. The $CO_2$ triggering limit can be a $CO_2$ partial pressure and/or a $CO_2$ partial volume, which is chosen to be so low that it is not reached by the fluctuations usually to be expected in the $CO_2$ content values in the plateau segment of an expiratory phase. For example, a suitable $CO_2$ triggering limit which leads to no or nearly no faulty triggering, can lie in the range from 5 to 20 mbar $CO_2$ partial pressure, preferably in the range from 7.5 to 15 mbar $CO_2$ partial pressure, especially preferably near 10 mbar $CO_2$ partial pressure.

The candidate interval thus defined can, based on at least one validation criterion, with little computing power and low memory space requirements, be very rapidly either validated as an examination time interval or discarded as a candidate interval.

As regards the validation, the evaluation device can be concretely designed to validate and use the candidate interval as the examination time interval, when the evaluation device ascertains in a validation procedure that during the candidate interval a $CO_2$ content value level which during an expiratory phase which includes at least the beginning of the candidate interval, or which prevails at the beginning of the candidate interval, decreases by at least a predetermined validation magnitude and/or by at least a predetermined validation fraction.

By using at least one of the, preferably all of the, aforementioned validation criteria it can be ensured that the examination time interval arising from the candidate interval through validation actually exhibits a sufficiently strong quantitative decrease in the $CO_2$ content values, in order to be able to determine a suitable, informative characteristic $CO_2$ gradient value in the examination time interval.

For example, a predetermined validation amount can represent a 2.25 vol % volume fraction, which in a standard atmosphere corresponds to about 23 mbar partial pressure. If, for example, within a candidate interval the $CO_2$ content value decreases by at least an amount which represents a 2.25 vol % volume fraction or 23 mbar partial pressure of carbon dioxide in the respiratory gas, then the candidate interval can be used as an examination time interval. A validation fraction, for instance 30%, can be utilized instead of the quoted quantitatively predetermined validation amounts. The validation fraction should be significantly greater than the usual fluctuation width of the $CO_2$ content value in the plateau segment of an expiratory phase in order to rule out a faulty validation as reliably as possible.

Since it is not to be expected that every first candidate interval will already become a valid examination time interval during a ventilation, the evaluation device is preferably designed to perform the validation procedure iteratively as from the triggering event, in each case with a modified candidate interval. The modification can, for example, consist in the modified candidate interval beginning later by a predetermined time increment relative to the immediately preceding discarded candidate interval. For example, a sequence of modified candidate intervals can begin at a temporal distance of an integral multiple of 10 ms from the triggering time point, where for example the multiple equals the current number of modifications of the candidate interval or the number of already discarded candidate intervals. The value of 10 ms is only given as an example. Instead, a value of 5 ms or 15 ms or 20 ms can also be used.

The validation magnitude and/or the validation fraction respectively can be different for different ventilation situations, for instance because the fluctuation width of the $CO_2$ content value in the plateau segments of the expiratory phases can vary from patient to patient or even during the ventilation of one and the same patient, depending on the latter's condition. So as to be able to take into account such change in the validation of candidate intervals, the evaluation device is preferably designed to ascertain the predetermined validation magnitude and/or the predetermined validation fraction on the basis of preceding $CO_2$ sensor signals, for instance on the basis of an average $CO_2$ content value level during a predetermined number of preceding expiratory plateau segments.

The respiratory gas source of the ventilation device can be a respiratory gas reservoir or a connector for connecting to such a reservoir, for instance a connector for connecting to an installed respiratory gas reservoir in a building, such as for instance of a clinic. For example, when ambient air is aspirated as the respiratory gas, the respiratory gas source can be a fan by means of which ambient air can be aspirated and conveyed into the ventilation line arrangement.

The pressure modification arrangement can comprise or be a valve, in particular a valve which is adjustable with respect to its feed-through cross-section. Additionally or alternatively, the pressure modification arrangement can comprise or be a fan through which respiratory gas can be conveyed into the ventilation line arrangement. In general, the pressure modification arrangement can be a conveyor with an aspiration side and a compression side. A fan can be both a respiratory gas source and a pressure modification arrangement.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
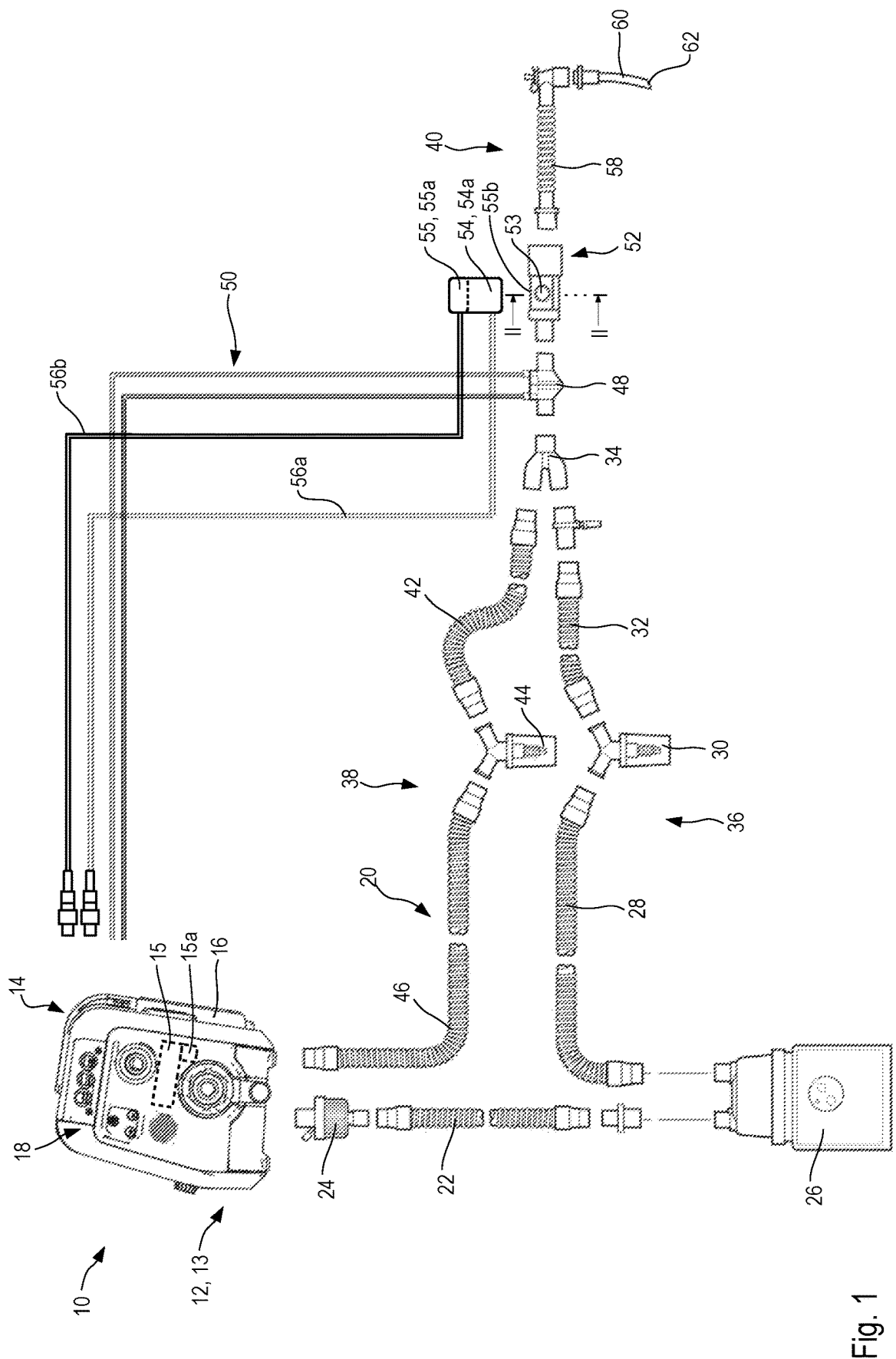
FIG. 1 A rough schematic exploded view of a ventilation device according to the invention, FIG. 2 A rough schematic sectional view through the measuring cuvette 52 of FIG. 1 along the sectional plane II-II of FIG. 1 which is orthogonal to the flow path SB of the measuring cuvette 52, FIG. 3A A rough schematic graphic depiction of a temporal course of a $CO_2$ partial pressure of respiratory gas flowing in the measuring cuvette 52 of FIG. 1, as it is detected during a ventilation operation by the $CO_2$ sensor assembly 54 in FIG. 1, with a normal measuring cuvette which is not humidity-loaded, FIG. 3B A rough schematic graphic depiction of a temporal course of an $O_2$ partial pressure of respiratory gas flowing in the measuring cuvette 52 of FIG. 1, as it is detected during a ventilation operation by the $O_2$ sensor assembly 55 in FIG. 1, with a normal measuring cuvette which is not humidity-loaded, FIG. 4A A rough schematic graphic depiction of a temporal course of a $CO_2$ partial pressure of respiratory gas flowing in the measuring cuvette 52 of FIG. 1, as it is detected during a ventilation operation by the $CO_2$ sensor assembly 54 in FIG. 1, with a measuring cuvette which is slightly humidity-loaded, FIG. 4B A rough schematic graphic depiction of a temporal course of an $O_2$ partial pressure of respiratory gas flowing in the measuring cuvette 52 of FIG. 1, as it is detected during a ventilation operation by the $O_2$ sensor assembly 55 in FIG. 1, with a measuring cuvette which is slightly humidity-loaded, FIG. 5A A rough schematic graphic depiction of a temporal course of a $CO_2$ partial pressure of respiratory gas flowing in the measuring cuvette 52 of FIG. 1, as it is detected during a ventilation operation by the $CO_2$ sensor assembly 54 in FIG. 1, with a measuring cuvette which is heavily humidity-loaded, and FIG. 5B A rough schematic graphic depiction of a temporal course of a $O_2$ partial pressure of respiratory gas flowing in the measuring cuvette 52 of FIG. 1, as it is detected during a ventilation operation by the $O_2$ sensor assembly 55 in FIG. 1, with a measuring cuvette which is heavily humidity-loaded.

Referring now to the drawings wherein the showings are for the purpose of illustrating preferred and alternative embodiments of the invention only and not for the purpose of limiting the same, in FIG. 1, an embodiment of a ventilation device according to the invention is labelled generally by 10. The ventilation device 10 comprises a respiratory gas source 12 in the form of a fan and a control device 14 for adjusting operational parameters of the respiratory gas source 12. The respiratory gas source 12 and the control device 14 are accommodated in the same housing 16. In this housing there are also situated valves which are known per se, such as an inspiratory valve and an expiratory valve. These, however, are not specifically depicted in FIG. 1.

The control device 14 comprises an evaluation device 15 for the processing of data-transmitting signals from sensor assemblies 54, 55, and also 48 which are elucidated in further detail below. For the storage of an operating program and for storage of data to be processed and of interim and final results of the data processing, the evaluation device 15 exhibits a data memory 15a which can be read and at least segment-wise written to by the evaluation device 15. The evaluation device 15 or parts thereof can be arranged in immediate proximity to at least one of the sensor assemblies 54, 55, and also 48. In the housings of sensor assemblies too, there can be accommodated specific components as intelligent sensor assemblies, such as microprocessors and memory units, for signal processing of the sensor signals of the respective sensor assembly.

The control device 14 of the ventilation device 10 exhibits an input/output device 18 comprising numerous switches, such as pushbutton switches and rotary switches, so as to be able to input data into the control device 14 as required. The fan of the respiratory gas source 12 can be modified in its conveying rate by the control device 14 in order to modify the quantity of respiratory gas which is conveyed by the respiratory gas source per unit of time. The respiratory gas source 12 is therefore, in the present embodiment example, also a pressure modification device 13 of the ventilation device 10.

To the respiratory gas source 12 there is connected a ventilation line arrangement 20, which in the present example comprises five flexible hoses. A first inspiratory ventilation hose 22 proceeds from a filter arranged between the respiratory gas source 12 and itself to a conditioning device 26, where the respiratory gas supplied by the respiratory gas source 12 is humidified to a predefined degree of humidity and as appropriate provided with aerosol medications. The filter 24 filters and cleans the ambient air supplied by the fan as the respiratory gas source 12.

A second inspiratory ventilation hose 28 leads from the conditioning device 26 to an inspiratory water trap 30. A third inspiratory ventilation hose 32 leads from the water trap 30 to a Y-connector 34 which connects the distal inspiratory line 36 and the distal expiratory line 38 into a combined proximal inspiratory-expiratory ventilation line 40.

From the Y-connector 34 back to the housing 16 there proceeds a first expiratory ventilation hose 42 to an expiratory water trap 44 and from there a second expiratory ventilation hose 46 to the housing 16, where the expiratory respiratory gas is released into the environment via a non-depicted expiratory valve.

On the proximal, i.e. patient-near, combined inspiratory-expiratory side of the Y-connector 34 there follows the Y-connector 34 immediately a flow sensor 48, here: a differential pressure flow sensor 48, which detects the inspiratory and expiratory flow of respiratory gas towards the patient and away from the patient. A line arrangement 50 transmits the gas pressure prevailing on both side of a flow obstruction in the flow sensor 48 to the control device 14, which from the transmitted gas pressures and in particular from the difference between the gas pressures calculates the quantity of inspiratory and expiratory respiratory gas flowing per unit of time.

In the direction away from the Y-connector 34 there follows towards the patient after the flow sensor 48 a measuring cuvette 52 both for non-dispersive infrared detection of a $CO_2$ fraction in the respiratory gas and for detecting an $O_2$ fraction in the respiratory gas through luminescence extinction. The $CO_2$ and the $O_2$ fractions both in the inspiratory respiratory gas and in the expiratory respiratory gas are thereby of interest, since the change in the $CO_2$ fraction between inspiration and expiration is a measure of the metabolizing competence of the patient's lung. In FIG. 1 there can be recognized one of the side windows 53, through which infrared light can be shone into the measuring cuvette 52 and/or emitted from the latter respectively, depending on the orientation of a multichannel infrared gas sensor 54*a* coupled detachably with the measuring cuvette as a $CO_2$ sensor assembly 54.

Figure 2:
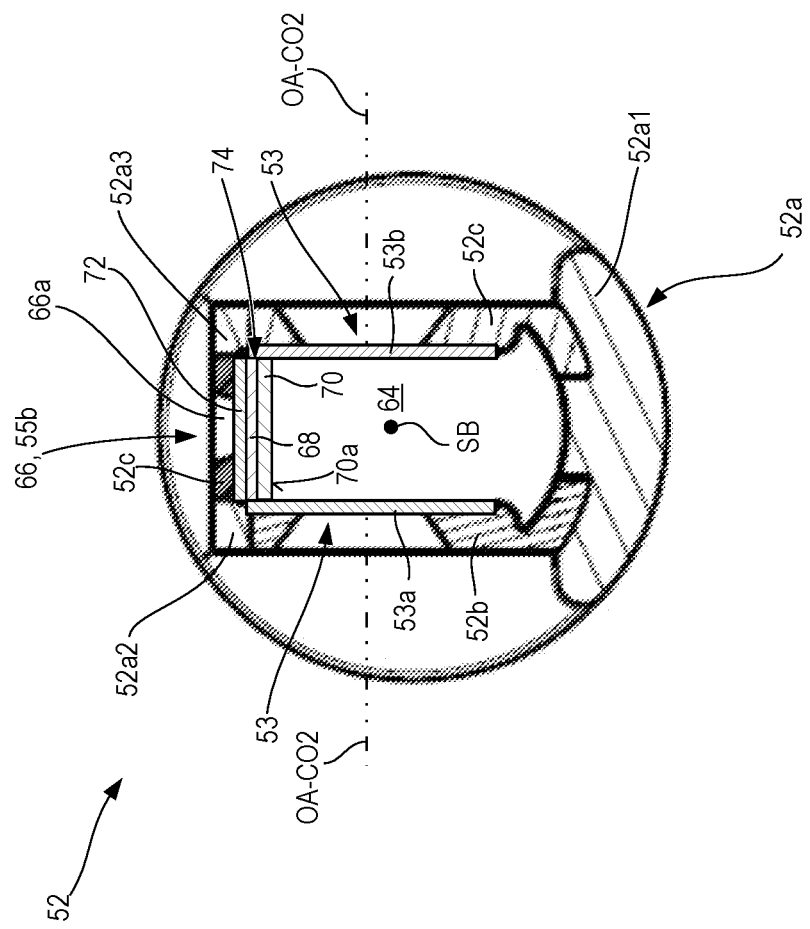

On the upper side of the $CO_2$ sensor assembly 54, preferably in a common sensor housing, there is situated a first, active part 55*a* of an $O_2$ sensor assembly 55, which in a manner known per se is designed to excite a luminophore-containing observation region 66 (s. FIG. 2) as a second, passive part 55*b* of the $O_2$ sensor arrangement 55 at the upper side of the measuring cuvette 52 by means of a radiation source to luminesce and to observe the luminescence behavior with regard to duration and/or intensity by means of a luminescence sensor.

The $CO_2$ sensor assembly 54 and the active part 55*a* of the $O_2$ sensor assembly 55 are couplable to the measuring cuvette 52 in such a way that the infrared gas sensor 54*b* can shine infrared light through the measuring cuvette 52 and that the active part 55*a* of the $O_2$ sensor assembly 55 can excite and observe the observation region 66 of the measuring cuvette 52. From the intensity of the infrared light, more precisely from its spectral intensity, it is possible to deduce in a manner known per se the quantity and/or fraction respectively of $CO_2$ in the respiratory gas flowing through the measuring cuvette 52, that is, its $CO_2$ content. $CO_2$ absorbs infrared light of a defined wavelength band. After passing through the measuring cuvette 52, the intensity of the infrared light at this wavelength depends essentially on the absorption of the infrared light of this wavelength by $CO_2$. A comparison of the intensity of the infrared light of the defined wavelength with a wavelength of the infrared light which does not belong to any absorption spectrum of a gas fraction to be expected in the respiratory gas, provides information about the fraction of $CO_2$ in the respiratory gas. The $CO_2$ sensor assembly 54 is therefore connected via a data cable 56*a* with the control device 14 of the ventilation device 10 and transmits via the data cable 56*a* the described intensity data to the control device 14 and/or to the evaluation device 15. As 'intensity information' there is deemed to be any information unambiguously related to the intensity of the infrared radiation, such as for instance a $CO_2$ content value ascertained from an infrared radiation intensity. In the case of the aforementioned 'intelligent' sensor assemblies, a first evaluation of the infrared signal can already take place, as described, in the evaluation device or part evaluation device in immediate proximity to the sensor assembly.

The active part 55*a* of the $O_2$ sensor assembly 55 excites the luminophore-containing observation region 66 of the measuring cuvette 52 to luminesce, where the luminescence is extinguished as a function of the quantity of oxygen reaching the excited luminophore. From the observed duration and intensity of the luminescence, therefore, it is possible to deduce the quantity or the fraction of $O_2$ in the respiratory gas, i.e. its $O_2$ content. The active part 55*a* of the $O_2$ sensor assembly 55 is, therefore, connected via a data cable 56*b* with the control device 14 and the evaluation device 15 and transmits via the data cable 56*b* data obtained from the observation of the luminescence behavior of the observation region 66 to the control device 14 and the evaluation device 15.

There follows after the measuring cuvette 52 in the direction towards the patient a further hose section 58, at which an endotracheal tube 60 is arranged as a ventilation interface to the patient. A proximal aperture 62 of the endotracheal tube 60 is both a respiratory gas outlet aperture, through which inspiratory respiratory gas is introduced through the endotracheal tube 60 into the patient, and a respiratory gas inlet aperture, through which expiratory respiratory gas is fed from the patient back into the endotracheal tube 60.

The difficulty underlying the present application is described below, using FIG. 2 as an example. FIG. 2 shows a section along the sectional plane II-II shown in FIG. 1 through the measuring cuvette 52 of FIG. 1, where the sectional plane II-II is oriented orthogonally to the drawing plane of FIG. 1 and hence also orthogonally to the flow path SB, along which a measurement chamber 64 has respiratory gas flowing through it bidirectionally in the ventilation operation.

The measurement chamber 64 is surrounded all around the flow path SB by the measuring cuvette 52, which for this purpose exhibits a preferably integrally injection-molded cuvette structure 52*a* with a bottom segment 52*a*1 and two frame struts 52*a*2 and 52*a*3 which are parallel to one another and to the flow path SB. Laterally, between the bottom segment 52*a*1 and each frame strut 52*a*2 and 52*a*3 there is in each case inset a side wall 52*b* or 52*c* respectively. On the side opposite the bottom segment 52*a*1 there is inset a ceiling wall 52*c* between the frame struts 52*a*2 and 52*a*3.

The sectional plane II-II proceeds through the windows 53, each of which is covered towards the measurement chamber 64 by a windowpane 53*a* and 53*b* transparent to infrared light. The windowpanes 53*a* and 53*b* can be made of a foil or of a dimensionally stable rigid material. The optical axis of the $O_2$ sensor assembly 54 lies in the sectional plane II-II and is indicated by the reference symbol OA-$CO_2$.

The upper side of the measuring cuvette 52 exhibits the observation region 66 already mentioned previously, at which when observed from outside the recess 66*a* is first noticeable, which penetrates through the ceiling wall 52*c*. Through the recess 66*a*, the luminophore of a luminophore layer 68 is excited to luminesce by the non-depicted radiation source. Through the recess 66*a*, besides, the luminescence behavior of the luminophore layer 68 after its excitation is detected by an appropriately designed luminescence sensor.

The luminophore layer 68 is carried by an oxygen-permeable membrane 70, namely only on the side of the membrane 70 facing away from the measurement chamber 64.

Such an oxygen-permeable membrane 70 can, for example, be made of polyvinylidene fluoride, PVDF for short. Towards the recess 66*a* the luminophore layer 68 is made of an oxygen-impermeable covering layer 72, for example out of biaxially oriented polypropylene.

In principle, this combined arrangement of a $CO_2$ sensor assembly 54 and an $O_2$ sensor assembly 55 including the laminate 74 belonging to the passive part 55b of the $O_2$ sensor assembly 55, consisting of the membrane 70, the luminophore layer 68, and the covering layer 72, functions well. It can, however, be the case that humidity carried along and/or body fluids, such as saliva or mucus, carried along by the respiratory gas flowing in the measurement chamber 64 precipitate on the side 70a of the membrane 70 facing towards the measurement chamber 64 and there form a liquid film covering the membrane 70 completely or in part. Due to the porosity of the membrane 70, liquid precipitating on the side 70a can also migrate into the membrane 70, thus modifying the oxygen permeability of the membrane 70.

If such precipitation takes place, respiratory gas and oxygen carried along by the respiratory gas reach the luminophore layer 68 only to a reduced extent, such that the luminescence extinction caused by the oxygen no longer describes correctly the true oxygen content of the respiratory gas.

Since the detection of the carbon dioxide in the respiratory gas relies on radiation absorption and not on molecular contact, the result of the carbon dioxide detection by the $CO_2$ sensor assembly 54 is, to the greatest extent possible, unaffected by liquid precipitating on the windowpanes 53a and 53b and/or can within certain limits be compensated for by using a reference radiation with a wavelength which is absorbed neither by the respiratory gas nor by the precipitated humidity.

The mode of operation of the ventilation device 10 for identifying an impairment of the $O_2$ sensor assembly 55, in particular of the luminophore layer 68, is elucidated below by reference to FIGS. 3A to 4B.

The data processing operations for determining an impairment of the $O_2$ sensor assembly 55 take place during the ongoing ventilation of a patient, but preferably are performed on $CO_2$ sensor signals and $O_2$ sensor signals saved in the data memory 15a and/or content values ascertained from these sensor signals respectively, such that within a plurality of data values available in a time interval it is possible to jump forward and back in time. Since during the determination of an impairment of the $O_2$ sensor assembly 55, the finite data memory 15a is written to with current sensor signals or content values formed therefrom, a resource-conserving determination of an impairment with the lowest possible demands on computing power and memory space is desirable in order to be able to perform the determination on the basis of available data before these are overwritten by more recent data. When overwriting data, the oldest stored data are always overwritten by the current data to be saved.

Figure 3A:
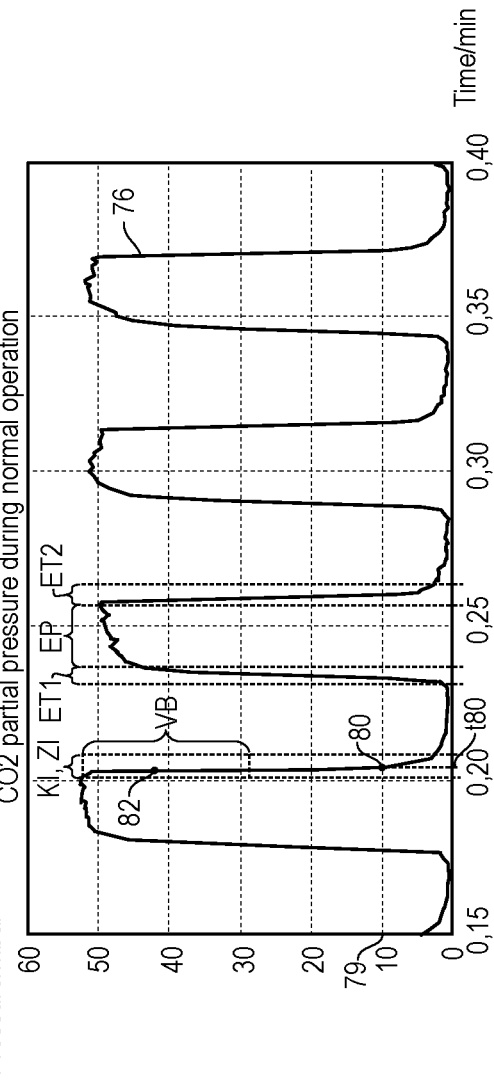

FIG. 3A shows in rough schematic form, in steps with a step width of 0.05 minutes, a temporal course 76 ascertained by the $CO_2$ sensor assembly 54 of the $CO_2$ partial pressure as a $CO_2$ content value under normal, in particular not liquid-loaded, operational conditions. Since ambient air supplied as respiratory gas contains almost no $CO_2$, the expiratory processes can be well distinguished from the inspiratory processes which exhibit a $CO_2$ partial pressure of below 5 mbar.

Figure 3B:
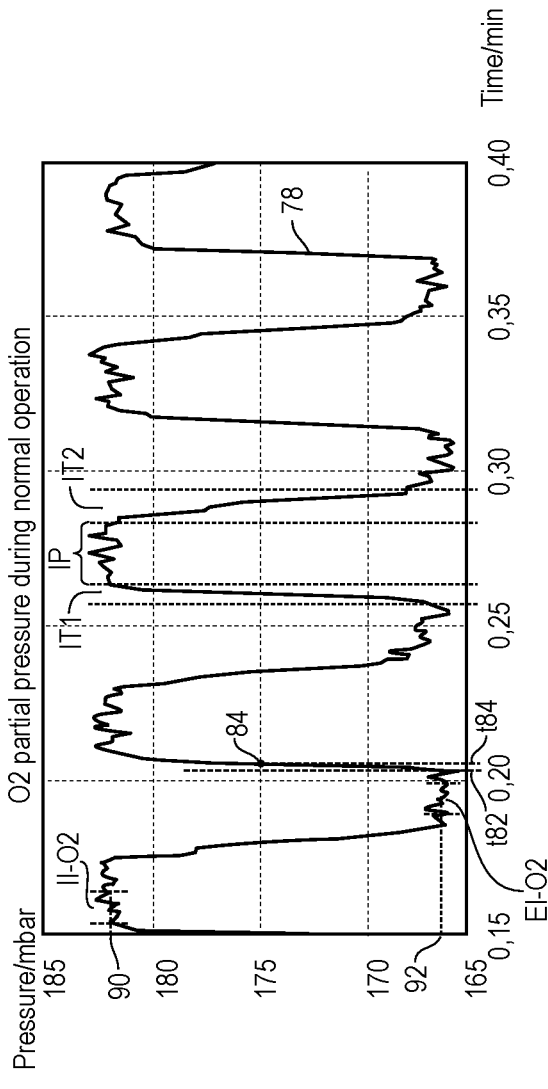

FIG. 3B shows in rough schematic form, to the same time scale as FIG. 3A, a temporal course 78, detected by the $O_2$ sensor assembly 55 during the detection of the $CO_2$ partial pressure, of an $O_2$ partial pressure in the respiratory gas, i.e. in ambient air, as an $O_2$ content value. Since during one breath only a part of the oxygen present in the ambient air is converted into $CO_2$ by the metabolism of the patient, the expiratory respiratory gas also still contains oxygen, but with a lower content. The temporal course 78 of the $O_2$ partial pressure, therefore, behaves qualitatively inversely to the temporal course 76 of the $CO_2$ partial pressure, in as much as the $O_2$ partial pressure takes on quantitatively higher values during an inspiratory process than during an expiratory process.

Since an inspiratory process begins by the respiratory gas source 12 beginning to supply to the patient inspiratory respiratory gas against the quantitatively decreasing flow of expiratory respiratory gas and since an expiratory process begins by respiratory gas which is under pressure beginning to flow out of the patient's lung away from the patient against the quantitatively decreasing flow of inspiratory respiratory gas, inspiratory and expiratory phases can overlap in time.

By reference to the second peak of the temporal course of the $CO_2$ partial pressure shown in FIG. 3A, the segments which such a temporal course exhibits during expiration are elucidated below.

In the changeover from inspiration to expiration, the flow direction of the respiratory gas necessarily changes in the ventilation line arrangement 20 and hence in the measuring cuvette 52, such that at the beginning of an expiration, starting from a flow velocity of approximately 0 m/s, the flow velocity of the expiratory respiratory gas and hence the volume and mass flow of expiratory respiratory gas increase, whereby the quantity of carbon dioxide carried along by the expiratory respiratory gas per unit of time into the measurement chamber 64 of the measuring cuvette 52 also increases. This increase in carbon dioxide content forms a first transient expiratory segment ET1.

To this first transient expiratory segment ET1 there adjoins an expiratory plateau segment EP, in which the change in the $CO_2$ partial pressure as the $CO_2$ content value chosen by way of an example is considerably smaller than in the first transient expiratory segment ET1. To the expiratory plateau segment EP there adjoins towards the end of the expiratory process a second transient expiratory segment ET2, in which the flow velocity and hence the mass and volume flow of expiratory respiratory gas decrease, in particular decrease down to 0 m/s. With the decreasing flow of expiratory respiratory gas, the quantity of carbon dioxide flowing per unit of time past the $CO_2$ sensor assembly 54 also necessarily decreases.

Likewise, the inspiratory processes exhibit at the beginning and at the end transient inspiratory segments IT1 and IT2, and between the transient segments an inspiratory plateau segment IP. These segments are depicted at the third peak in FIG. 3B. The time fractions of an inspiration phase which fall on the individual segments IT1, IP, and IT2 can differ from the time fractions of the respective segments ET1, EP, and ET2 of an expiration phase and normally are different because of the different fluid-mechanical processes and their causes.

Since the ventilation device 10 preferably uses both the gradient criterion and the difference criterion, the ventilation device 10 begins by determining a characteristic $CO_2$ gradient value, since the latter preferably serves as a reference point for further determinations of values. It should, however, be pointed out that as elucidated in the introduction to the description, the further values described below can also be determined without previously determining a characteristic $CO_2$ gradient value.

In experiments conducted thus far, the value of the quantitatively largest possible slope of the temporal course of the $CO_2$ partial pressure (or generally, of a $CO_2$ content value) in the falling flank of an expiratory phase has proved to be the most informative characteristic $CO_2$ gradient value. First of all, the evaluation device 15 determines as effectively as possible and at little computational cost a candidate interval KI in which the falling flank of the $CO_2$ partial pressure could lie in an expiratory phase. For example, for the second peak in FIG. 3A this can be the second transient segment ET2 indicated there.

One of several possible forms of the determination of a candidate interval KI, which has proved reliable in experiments conducted thus far, comprises first of all determining that point in time at which the $CO_2$ content value has decreased to a predetermined level which reliably no longer belongs to the expiratory plateau segment EP, for example at which the $CO_2$ partial pressure has fallen below a $CO_2$ triggering limit 79 of 20 mbar or even of 10 mbar. In FIG. 3A, the $CO_2$ triggering limit 79 of 10 mbar is used, which in the first expiratory process is fallen below at the point 80. It lies at approximately 0.204 minutes.

Starting from the triggering event thus ascertained of falling below the predefined $CO_2$ triggering limit 79, the candidate interval KI is defined from the starting point in time t80, i.e. in the example 0.204 minutes, which begins a predetermined first time interval before the triggering time point t80 and ends a predetermined second time interval after the triggering time point t80. The predetermined first and second time intervals are chosen, based on experience gained thus far in ventilation operations, in such a way that the falling flank lies in the candidate interval KI in at least 85%, preferably in at least 95% of the expiratory phases.

The evaluation device 15 subsequently verifies whether the candidate interval KI is a valid examination time interval ZI, by checking whether the $CO_2$ content value, starting from the $CO_2$ content value prevailing at the beginning of the candidate interval KI, decreases within the candidate interval KI by at least a predetermined validation magnitude VB of 23 mbar. Since this is the case in the depicted candidate interval KI, the candidate interval KI is validated as an examination time interval ZI. From now on it is used as examination time interval ZI. As elucidated in the introduction to the description, other validation criteria can additionally or alternatively be utilized for validating the candidate interval KI.

Within the examination time interval ZI thus defined, the evaluation device 15 determines, for example through iterative forming of differences between two $CO_2$ partial pressure values lying at a distance of $\Delta t$ and through division of the difference thus formed by the temporal distance $\Delta t$, a sequence of $CO_2$ partial pressure gradient values and selects therefrom the quantitatively largest. In the depicted example it lies at point 82.

Subsequently the point in time t82 at which the quantitatively largest $CO_2$ partial pressure gradient value occurs, is used as a reference point in time. By adding a predetermined positive time interval to the reference point in time t82, the later point in time t84 is obtained which lies in the rising flank of the second peak of the graph 78.

The magnitude of the slope of the graph 78 as the $O_2$ gradient value is ascertained at the point in time t84 thus obtained. This is the slope of the graph 78 at the point 84. For applying the gradient criterion, the point 84 does not have to be a key point on the graph 78. It suffices that this point 84 lies the predetermined time interval away from the reference point in time t82 in the rising flank of the temporal course of the $O_2$ content values. The predetermined time interval is chosen in such a way that in at least 85%, preferably at least 95%, especially preferably in 100% of the inspiratory processes it lies in the rising flank of the temporal course of the $O_2$ content value, which is already possible due to the fact that by virtue of the mechanical ventilation of the patient, inspiratory processes follow expiratory processes directly and predictably.

The evaluation device 15 then forms a ratio of the magnitudes of the two obtained gradient values: $CO_2$ gradient value and $O_2$ gradient value, as a change ratio of the magnitudes of the gradient values, and compares the value of the change ratio thus determined with a predetermined change ratio limit stored in the data memory 15a. When the ratio of the magnitudes, with the $CO_2$ gradient value in the numerator and the $O_2$ gradient value in the denominator, is larger than the change ratio limit previously determined in the laboratory, which for example can equal 16.6, the evaluation device 15 outputs a signal which indicates that the $O_2$ sensor assembly 55 and with it the obtained $O_2$ sensor signals are degraded. This is not the case here in FIGS. 3A and 3B.

Additionally to the gradient criterion described previously, the evaluation device 15 uses the difference criterion described above in the introduction to the description. To this end, in FIG. 3B the difference is formed between a characteristic inspiratory $O_2$ content value, i.e. here an $O_2$ partial pressure, and a characteristic expiratory $O_2$ content value (partial pressure). For this purpose there can be determined, for example, starting from the already determined reference point in time t82, an inspiratory time interval II-$O_2$ lying at a predetermined temporal distance in respect of its start and its end relative to the reference point in time t82, and an expiratory time interval EI-$O_2$ likewise lying at a predetermined temporal distance in respect of its start and its end relative to the reference point in time t82. From the $O_2$ content values lying with the intervals II-$O_2$ and EI-$O_2$ there can respectively be ascertained an average $O_2$ content value as the characteristic inspiratory $O_2$ content value and the characteristic expiratory $O_2$ content value. The characteristic inspiratory $O_2$ content value is preferably ascertained in the inspiratory process which immediately precedes the expiratory process in which the characteristic $CO_2$ gradient value is ascertained.

In the example depicted in FIG. 3B, there is obtained for the characteristic inspiratory $O_2$ content value in the predetermined inspiratory time interval II-$O_2$ an averaged inspiratory $O_2$ content value of about 182 mbar indicated by the reference symbol 90. For the characteristic expiratory $O_2$ content value in the predetermined expiratory time interval EI-$O_2$, there is obtained an averaged expiratory $O_2$ content value of about 166.3 mbar indicated by the reference symbol 92. The $O_2$ difference value consequently equals about 15.7 mbar. For the atmosphere with an ambient pressure of 1013 mbar present in the example, the atmosphere-based $O_2$ difference value is about 0.015. The evaluation device 15 compares this atmosphere-based $O_2$ difference value with an $O_2$ difference limit which was determined in the laboratory in advance. The latter can, for example, be 0.01. If the atmosphere-based $O_2$ difference value falls below the $O_2$ difference limit, then the difference criterion for a signal output is satisfied for the atmosphere-based $O_2$ difference value. This is not the case here.

Consequently, the evaluation device 15 assesses the $O_2$ sensor assembly 55 as not impaired and therefore does not output a signal indicating an impairment of the $O_2$ sensor assembly 55.

FIGS. 4A and 4B show a temporal course of the $CO_2$ partial pressure and of the $O_2$ partial pressure during ventilation of the same patient with the same ventilation parameters. However, in the meantime a little liquid has precipitated on the walls bordering the measurement chamber 64, consequently also on the windows 53 and on the membrane 70 of the $O_2$ sensor assembly 55.

The evaluation device 15 performs on the sensor signals and on the content values ascertained therefrom the same operations as were elucidated previously in connection with FIGS. 3A and 3B. Equal and significance-equivalent values and regions as in FIGS. 3A and 3B are indicated in FIGS. 4A and 4B by the same reference symbols, to which an apostrophe is added merely for the purpose of distinguishing the wet state of the $O_2$ sensor assembly 55 from the previously discussed dry state. Consequently, the procedure described previously by reference to FIGS. 3A and 3B for determining an impairment of the $O_2$ sensor assembly 55, also applies to the data and data courses of FIGS. 4A and 4B.

It is important here that the falling flank of the temporal course 76' of the $CO_2$ partial pressures in the liquid-loaded measuring cuvette 52 exhibits an approximately identical slope as previously in the dry measuring cuvette 52. The characteristic $CO_2$ gradient value at the point in time t82', ascertained at the point 82' as the quantitatively largest 'wet' $CO_2$ gradient value in the examination time interval ZI', is quantitatively approximately equal to the 'dry' $CO_2$ gradient value previously ascertained at point 82.

In contrast, the course of the rising flank of the $O_2$ gradient values is flatter, such that the 'wet' $O_2$ gradient value, ascertained at the point in time t84' as a function of the reference point in time t82', as previously, exhibits a quantitatively smaller value.

The change ratio, ascertained with the data shown in FIGS. 4A and 4B as the ratio of the magnitudes of the $CO_2$ gradient value in the numerator and the $O_2$ gradient value in the denominator, becomes quantitatively larger and now exceeds the predetermined change ratio limit of 16.6. The evaluation device 15 therefore deduces a degradation of the $O_2$ sensor assembly 55 and outputs a corresponding signal.

Alternatively to an immediate output of the signal, the evaluation device can also output the signal, for example, only if within five consecutive breaths for each breath at least one criterion out of the gradient criterion and difference criterion is satisfied.

In the example depicted in FIG. 4B, there is obtained for the characteristic inspiratory $O_2$ content value in the predetermined inspiratory time interval II-$O_2$ an averaged inspiratory $O_2$ content value, determined as described above and indicated by the reference symbol 90', of about 181.5 mbar. As the characteristic expiratory $O_2$ content value 92', determined as described above, there is obtained an averaged expiratory $O_2$ content value of about 166.7 mbar. The $O_2$ difference value consequently equals about 14.8 mbar. The atmosphere-based $O_2$ difference value in the atmosphere present in the example, with an ambient pressure of 1013 mbar, equals about 0.014. The evaluation device compares this atmosphere-based $O_2$ difference value with the aforementioned $O_2$ difference limit of 0.01.

The gradient criterion is satisfied, but the difference criterion is not. This can be down to the relatively low quantity of precipitated humidity in the example of FIGS. 4A and 4B. To determine an impairment of the $O_2$ sensor assembly 55, however, satisfying one of the indicated criteria is already sufficient.

Figure 5A:
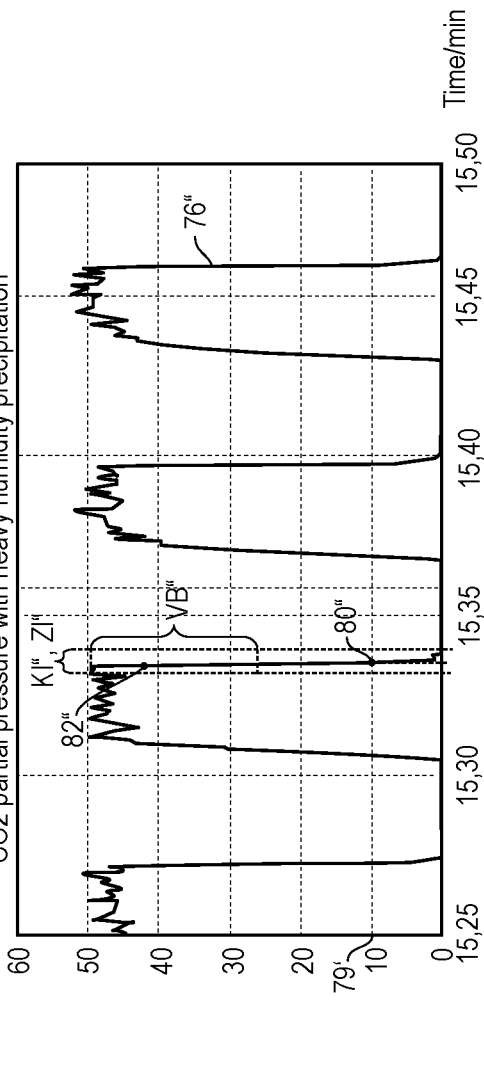
Figure 5B:
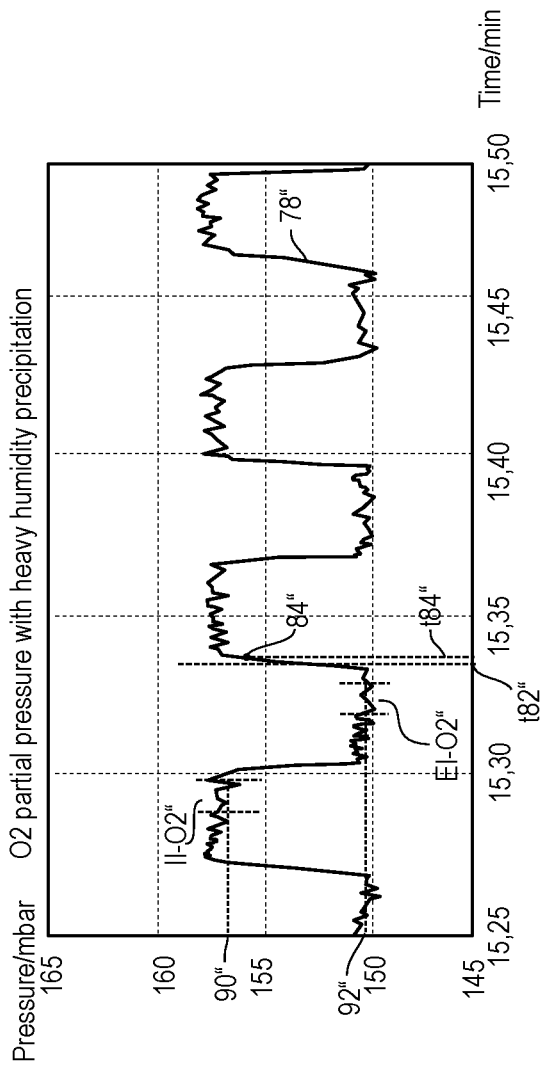

FIGS. 5A and 5B show, in analogy with FIGS. 4A and 4B, $CO_2$ and $O_2$ content values respectively as a function of time, with an $O_2$ sensor assembly 55 which is more heavily contaminated with liquid than is the case in the example of FIGS. 4A and 4B. The diagrams in FIGS. 5A and 5B are based on detection of respiratory gas in a measuring cuvette 52 whose inner surface is covered with a layer of mucus. This also applies to the surface 70a of the membrane 70 facing towards the measurement chamber 64. Equal and significance-equivalent values and regions as in FIGS. 3A to 4B are indicated by the same reference symbols, but identified by a double apostrophe. Consequently, the liquid loading of the $O_2$ sensor assembly 55 increases with increasing number of apostrophes.

Once again, the data operations elucidated by reference to FIGS. 3A and 3B are performed on the $CO_2$ and $O_2$ content values, in order to assess whether or not the $O_2$ sensor assembly 55 is impaired.

Based on the example of FIGS. 5A and 5B, the difference criterion shall first of all be elucidated by reference to an example. As FIG. 5B shows, due to the heavier liquid loading than in the case of FIG. 4B, the level of the $O_2$ partial pressure in the inspiratory plateau segment has decreased from about between 181.5 and 182 mbar to about 167 mbar. Likewise, the level of the $O_2$ partial pressure in the expiratory plateau segment has decreased from about 167 mbar to about 151 mbar.

The ratio of inspiratory to expiratory mean $O_2$ partial pressure in the plateau segments of the $O_2$ partial pressure curves 78' and 78" of the liquid-loaded $O_2$ sensor assembly 55 lies in both cases at about 1.1. This applies likewise to the $O_2$ partial pressure curve 78 of the not liquid-loaded $O_2$ sensor assembly 55 of FIG. 3B.

By comparing FIGS. 4B and 5B it becomes clear that with increasing liquid loading of the $O_2$ sensor assembly 55, a state could be reached in which the rising flank of an $O_2$ partial pressure curve can turn out so short in the changeover segment during the transition from an expiratory phase to an inspiratory phase that an informative $O_2$ gradient value at this flank can no longer be reliably determined. Then the $O_2$ gradient criterion could risk failing.

In the present case, the gradient criterion is also satisfied in the liquid-loaded $O_2$ sensor assembly 55 which leads to the content values of FIGS. 5A and 5B.

Additionally at the $O_2$ partial pressure curve 78" of FIG. 5B too, as already elucidated previously by reference to FIGS. 3B and 4B, there is defined an inspiratory phase segment II-O2" for ascertaining the characteristic inspiratory $O_2$ content value 90" and an expiratory phase segment EI-O2" for ascertaining the characteristic expiratory $O_2$ content value 92".

The ventilation frequency in FIGS. 5A and 5B is somewhat lower than in the preceding FIGS. 3A to 4B, which is why the evaluation device 15 has adjusted the temporal distances of the beginning and the end of the respiratory part-phase segments II-O2" and EI-O2" from the reference point in time t82" through a minor increase. It is, however, equally possible to define the beginning and the end of the respiratory part-phase segments II-O2" and EI-O2" such that the respiratory part-phase segments II-O2" and EI-O2" lie in the plateau segments for all reasonably to be expected breathing frequencies during the operation of the ventilation device 10. The respiratory part-phase segments II-O2" and EI-O2" can turn out, for this purpose, shorter than depicted.

In the first inspiratory phase in FIG. 5B, in which the inspiratory phase segment II-O2" is indicated, there is obtained an $O_2$ content value arithmetically averaged over the inspiratory phase segment II-O2" as the characteristic inspiratory content value 90" of 156.8 mbar. In the following expiratory phase segment EI-O2", there is obtained an $O_2$ content value arithmetically averaged over the expiratory phase segment EI-O2" as the characteristic expiratory content value 92" of about 150.4 mbar. From this there is obtained an $O_2$ difference value of 6.4 mbar, that is to say, an atmosphere-based $O_2$ difference value of 0.006. The atmospheric pressure of 1013 mbar is unchanged.

The evaluation device 15 compares the ascertained atmosphere-based $O_2$ difference value of 0.006 with the $O_2$ difference limit of 0.01 already quoted above and determines that the ascertained atmosphere-based $O_2$ difference value is smaller than the predetermined $O_2$ difference limit. The difference criterion is consequently satisfied in addition to the gradient criterion. The evaluation device 15 outputs, in the case of the ventilation situation of FIGS. 5A and 5B too, a signal which indicates a degradation of the $O_2$ sensor assembly 55.

It should be added that the inspiratory phase segments and expiratory phase segments identified above can also be utilized for ascertaining characteristic inspiratory $CO_2$ content values and characteristic expiratory $CO_2$ content values. These characteristic $CO_2$ content values too, can be values arithmetically averaged over their associated respiratory part-phase segment. A $CO_2$ difference value can be calculated on the basis of at least one characteristic expiratory $CO_2$ content value and at least one characteristic inspiratory $CO_2$ content value, for instance as the magnitude of the difference between the characteristic content values. The aforementioned validation magnitude and/or the validation fraction can be ascertained on the basis of the $CO_2$ difference value thus obtained. For example, the validation magnitude can be a predetermined fraction of the $CO_2$ difference value. The validation fraction in percent can be determinable as a function of the $CO_2$ difference value, for instance by storing a table or a characteristic diagram of validation fractions as a function of the $CO_2$ difference value.

Even though the respiratory part-phase segments can be the same for determining characteristic content values of $O_2$ and $CO_2$, it should not be ruled out that different respiratory part-phase segments are determined for each respiratory gas component: $O_2$ and $CO_2$, for instance due to different predetermined temporal distances of the beginning and the end of a respiratory part-phase segment from a reference point in time, such as the point in time of the occurrence of the quantitatively largest temporal change in the $CO_2$ content value. The reference point in time preferably lies in a changeover segment in the transition from an expiratory phase to an inspiratory phase.

What has been said in the present application regarding the determination of characteristic inspiratory and expiratory $O_2$ content values, also applies mutatis mutandis to characteristic inspiratory and expiratory $CO_2$ content values with the stipulation that $O_2$ should be replaced by $CO_2$.

It is clear that the verification procedures which the evaluation device performs on the data transmitted by the sensor signals, were elucidated above merely by way of example on the basis of graphic representations of these data. The verification procedures are, however, performed on numerical values and/or numerical value-pairs respectively or generally on linked numerical values.

Any value which stands in an unambiguous functional relationship with a content value addressed in the present application is equivalent to the content value.

The present invention allows a degradation of the $O_2$ sensor assembly 55 to be recognized promptly without additional sensors.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A ventilation device for artificial respiration comprising:
   a respiratory gas source,
   a ventilation line arrangement in order to lead inspiratory respiratory gas from the respiratory gas source to a patient-side proximal respiratory gas outlet aperture and in order to lead expiratory respiratory gas away from a proximal respiratory gas inlet aperture,
   a pressure modification arrangement for modifying the pressure of the respiratory gas flowing in the ventilation line arrangement,
   a control device configured to control the operation of the respiratory gas source and/or of the pressure modification arrangement,
   an evaluation device for processing sensor signals, and
   an O2 sensor assembly for ascertaining an O2 content value which represents an oxygen content of the respiratory gas flowing in the ventilation line arrangement, where the O2 sensor assembly outputs to the evaluation device O2 sensor signals which contain information about the O2 content value,
   where the evaluation device is configured to determine on a basis of the O2 sensor signals an O2 change value which represents a change in the O2 content value and when the O2 change value satisfies a predetermined condition to deduce a degradation of the O2 sensor assembly and output a signal, wherein the evaluation device is configured to ascertain, as the O2 change value, an O2 difference value which represents a quantitative difference between a characteristic expiratory O2 content value of the expiratory respiratory gas and a characteristic inspiratory O2 content value of the inspiratory respiratory gas, where the predetermined condition is that the O2 difference value is related in a predetermined relative relationship to an O2 difference limit.

2. The ventilation device according to claim 1, wherein the evaluation device is configured to output the signal only if the predetermined condition is satisfied a predetermined plurality of times within a predetermined plurality of breaths.

3. The ventilation device according to claim 1, wherein the evaluation device is configured to take into account, when performing the comparisons of O2 difference values with the O2 difference limit, at least one atmospheric state value which represents a state of the ambient atmosphere of the ventilation device.

4. The ventilation device according to claim 3, wherein the evaluation device is configured to ascertain the O2 difference limit as a function of the at least one atmospheric state value, or is configured to ascertain from the O2 difference value and the at least one atmospheric state value an atmosphere-based O2 difference value.

5. The ventilation device according to claim 3, wherein the at least one atmospheric state value represents the atmospheric pressure, that the $O_2$ difference value represents an $O_2$ partial pressure difference value between an $O_2$ partial pressure in the expiratory respiratory gas and an $O_2$ partial pressure in the inspiratory respiratory gas.

6. The ventilation device according to claim 1, wherein the characteristic inspiratory O2 content value derives from an inspiratory phase segment which is located at a first temporal distance from a beginning of an inspiratory phase and a second temporal distance from an end of the inspiratory phase, and/or that the characteristic expiratory O2 content value derives from an expiratory phase segment which is located at a third temporal distance from a beginning of an expiratory phase and at a fourth temporal distance from an end of the expiratory phase.

7. The ventilation device according to claim 6, wherein the evaluation device is configured to identify the inspiratory phase segment and/or the expiratory phase segment and to ascertain a characteristic inspiratory O2 content value and/or a characteristic expiratory O2 content value, respectively.

8. The ventilation device according to claim 7, wherein the ventilation device comprising a CO2 sensor assembly which is configured to ascertain a CO2 content value representing a carbon dioxide content of the respiratory gas flowing in the ventilation line arrangement, where the CO2 sensor assembly outputs to the evaluation device CO2 sensor signals which contain information about the CO2 content value and wherein the evaluation device is configured to ascertain, on a basis of a plurality of CO2 sensor signals of a breath, the quantitatively largest temporal change in the CO2 content value towards decreasing values, where the evaluation device is further configured to identify the inspiratory phase segment and/or the expiratory phase segment as a function of the temporal determination of the occurrence of the quantitatively largest temporal change in the CO2 content value towards decreasing values.

9. The ventilation device according to claim 6, wherein the ventilation device comprising a CO2 sensor assembly which is configured to ascertain a CO2 content value representing a carbon dioxide content of the respiratory gas flowing in the ventilation line arrangement, where the CO2 sensor assembly outputs to the evaluation device CO2 sensor signals which contain information about the CO2 content value and wherein the evaluation device forms the characteristic inspiratory O2 content value as an average over a plurality of O2 sensor signals in the inspiratory phase segment and/or that the evaluation device forms the characteristic expiratory O2 content value as an average over a plurality of O2 sensor signals in the expiratory phase segment.

10. The ventilation device according to claim 1, wherein the ventilation device comprising a CO2 sensor assembly which is configured to ascertain a CO2 content value representing a carbon dioxide content of the respiratory gas flowing in the ventilation line arrangement, where the CO2 sensor assembly outputs to the evaluation device CO2 sensor signals which contain information about the CO2 content value.

11. A ventilation device for artificial respiration comprising:
a respiratory gas source,
a ventilation line arrangement in order to lead inspiratory respiratory gas from the respiratory gas source to a patient-side proximal respiratory gas outlet aperture and in order to lead expiratory respiratory gas away from a proximal respiratory gas inlet aperture,
a pressure modification arrangement for modifying the pressure of the respiratory gas flowing in the ventilation line arrangement,
a control device configured to control the operation of the respiratory gas source and/or of the pressure modification arrangement,
an evaluation device for processing sensor signals, and
an O2 sensor assembly for ascertaining an O2 content value which represents an oxygen content of the respiratory gas flowing in the ventilation line arrangement, where the O2 sensor assembly outputs to the evaluation device O2 sensor signals which contain information about the O2 content value,
where the evaluation device is configured to determine on a basis of the O2 sensor signals an O2 change value which represents a change in the O2 content value and when the O2 change value satisfies a predetermined condition to deduce a degradation of the O2 sensor assembly and output a signal, wherein the ventilation device comprising a CO2 sensor assembly which is configured to ascertain a CO2 content value representing a carbon dioxide content of the respiratory gas flowing in the ventilation line arrangement, where the CO2 sensor assembly outputs to the evaluation device CO2 sensor signals which contain information about the CO2 content value, wherein the evaluation device is configured to ascertain from the CO2 sensor signals a CO2 gradient value representing a temporal change in the CO2 content value in the expiratory respiratory gas, and that the evaluation device is further configured to ascertain, as the O2 change value, an O2 gradient value representing a temporal change in the O2 content value in the inspiratory respiratory gas, where the predetermined condition is that a ratio of the CO2 gradient value to the O2 gradient value is related in a predetermined relative relationship to a change ratio limit.

12. The ventilation device according to claim 11, wherein the evaluation device is configured to ascertain, on a basis of a plurality of CO2 sensor signals of a breath, a quantitatively largest temporal change in the CO2 content value towards decreasing values as the CO2 gradient value.

13. The ventilation device according to claim 12, wherein the evaluation device is configured to use a point in time of an occurrence of the CO2 gradient value as a reference point in time and on a basis of a plurality of O2 sensor signals of a breath to use a change value of the O2 content value as the O2 gradient value which occurs at a predetermined temporal distance from the CO2 gradient value.

14. The ventilation device according to claim 13, wherein the predetermined temporal distance is chosen in such a way that the $O_2$ gradient value lies in a segment of a changeover from an expiratory phase to an inspiratory phase with the oxygen contents increasing with time.

15. The ventilation device according to claim 14, wherein the CO2 gradient value lies in a segment of a changeover from an expiratory phase to an inspiratory phase, where the predetermined temporal distance lies in a range from 25 to 80 ms, or in a range from 35 to 65 ms, or in a range from 45 to 55 ms.

16. The ventilation device according to claim 15, wherein the O2 gradient value lies in an inspiratory process which immediately follows the expiratory process in which the CO2 gradient value lies.

17. The ventilation device according to claim 12, wherein the evaluation device is configured to identify an examination time interval in a phase of a changeover from an expiratory process to an inspiratory process and to search only within the examination time interval for an occurrence of the quantitatively largest temporal change in the CO2 content value towards decreasing CO2 content values.

18. The ventilation device according to claim 17, wherein the evaluation device, in order to identify the examination time interval from a plurality of $CO_2$ sensor signals as a triggering event, determines when the $CO_2$ content value falls below a predetermined $CO_2$ triggering limit, and starting from the ascertained triggering time event defines a time interval as a candidate interval.

19. The ventilation device according to claim 18, wherein the evaluation device is configured to use the candidate interval as the examination time interval, when the evaluation device ascertains in a validation procedure that during the candidate interval a $CO_2$ content value level which during an expiratory phase which includes at least the beginning of the candidate interval, or the $CO_2$ content value level which prevails at the beginning of the candidate interval, decreases by at least a predetermined validation magnitude and/or by at least a predetermined validation fraction.

20. The ventilation device according to claim 19, wherein the evaluation device is configured to perform the validation procedure iteratively from the triggering event for a plurality of iterations, in each iterations with a modified candidate interval.

21. The ventilation device according to claim 19, wherein the evaluation device is configured to ascertain the predetermined validation magnitude and/or the predetermined validation fraction on a basis of $CO_2$ sensor signals preceding the $CO_2$ sensor signals.

22. The ventilation device according to claim 11, wherein the evaluation device is configured to output the signal only if the predetermined condition is satisfied a predetermined plurality of times within a predetermined plurality of breaths.

* * * * *